(12) United States Patent
Karicherla et al.

(10) Patent No.: US 12,251,223 B2
(45) Date of Patent: Mar. 18, 2025

(54) IMPLANTABLE MEDICAL DEVICES WITH MICROFABRICATED LEADS

(71) Applicant: Verily Life Sciences LLC, South San Francisco, CA (US)

(72) Inventors: Annapurna Karicherla, South San Francisco, CA (US); Bo Lu, South San Francisco, CA (US); Cindy Au, South San Francisco, CA (US); Brian Pepin, South San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 700 days.

(21) Appl. No.: 17/279,004

(22) PCT Filed: Sep. 24, 2019

(86) PCT No.: PCT/US2019/052556
§ 371 (c)(1),
(2) Date: Mar. 23, 2021

(87) PCT Pub. No.: WO2020/068722
PCT Pub. Date: Apr. 2, 2020

(65) Prior Publication Data
US 2022/0031214 A1  Feb. 3, 2022

Related U.S. Application Data

(60) Provisional application No. 62/737,371, filed on Sep. 27, 2018.

(51) Int. Cl.
*A61B 5/25* (2021.01)
*A61B 5/24* (2021.01)
(Continued)

(52) U.S. Cl.
CPC .............. *A61B 5/25* (2021.01); *A61N 1/0556* (2013.01); *A61B 5/0004* (2013.01);
(Continued)

(58) Field of Classification Search
CPC ....... A61B 5/25; A61B 5/0004; A61B 5/0006; A61B 5/004; A61B 5/0042; A61B 5/0082;
(Continued)

(56) References Cited

U.S. PATENT DOCUMENTS 5,057,092 A    10/1991  Webster
6,213,995 B1 *  4/2001  Steen ............... A61B 18/14
                                                    604/527
(Continued)

FOREIGN PATENT DOCUMENTS

CN    102186534 A    9/2011
CN    106163432 A    11/2016
(Continued)

OTHER PUBLICATIONS

Application No. PCT/US2019/052556, International Search Report and Written Opinion, Mailed on Dec. 5, 2019, 14 pages.
(Continued)

*Primary Examiner* — Eun Hwa Kim
*Assistant Examiner* — Ana Veruska Guerrero
(74) *Attorney, Agent, or Firm* — Kilpatrick Townsend & Stockton LLP

(57) ABSTRACT

Embodiments relate to an implantable device. Specifically, a device includes a flexible connection component that includes a set of conductive filaments that connect a set of electrodes (or traces connected to the electrodes) and circuitry that receives and/or transmits electronic signals from and/or to the electrodes.

18 Claims, 4 Drawing Sheets

(51) Int. Cl.
| | | |
|---|---|---|
| *A61B 5/273* | (2021.01) | |
| *A61N 1/05* | (2006.01) | |
| *A61B 5/00* | (2006.01) | |
| *A61B 5/0215* | (2006.01) | |
| *A61B 5/05* | (2021.01) | |
| *A61B 5/1473* | (2006.01) | |
| *A61B 5/263* | (2021.01) | |
| *A61B 5/265* | (2021.01) | |
| *A61B 5/268* | (2021.01) | |
| *A61B 5/271* | (2021.01) | |
| *A61B 5/282* | (2021.01) | |
| *A61B 5/283* | (2021.01) | |
| *A61B 5/291* | (2021.01) | |
| *A61B 5/293* | (2021.01) | |
| *A61B 5/31* | (2021.01) | |
| *A61B 5/316* | (2021.01) | |
| *A61B 5/333* | (2021.01) | |
| *A61B 5/335* | (2021.01) | |
| *A61B 5/369* | (2021.01) | |
| *A61B 5/372* | (2021.01) | |
| *A61N 1/04* | (2006.01) | |
| *A61N 1/08* | (2006.01) | |

(52) U.S. Cl.
CPC ............ *A61B 5/0006* (2013.01); *A61B 5/004* (2013.01); *A61B 5/0042* (2013.01); *A61B 5/0082* (2013.01); *A61B 5/0084* (2013.01); *A61B 5/0215* (2013.01); *A61B 5/05* (2013.01); *A61B 5/1473* (2013.01); *A61B 5/24* (2021.01); *A61B 5/263* (2021.01); *A61B 5/265* (2021.01); *A61B 5/268* (2021.01); *A61B 5/271* (2021.01); *A61B 5/273* (2021.01); *A61B 5/282* (2021.01); *A61B 5/283* (2021.01); *A61B 5/291* (2021.01); *A61B 5/293* (2021.01); *A61B 5/31* (2021.01); *A61B 5/316* (2021.01); *A61B 5/333* (2021.01); *A61B 5/335* (2021.01); *A61B 5/369* (2021.01); *A61B 5/372* (2021.01); *A61B 5/6867* (2013.01); *A61B 5/6868* (2013.01); *A61B 2562/125* (2013.01); *A61N 1/04* (2013.01); *A61N 1/042* (2013.01); *A61N 1/0526* (2013.01); *A61N 1/0529* (2013.01); *A61N 1/08* (2013.01)

(58) Field of Classification Search
CPC ....... A61B 5/0084; A61B 5/0215; A61B 5/05; A61B 5/1473; A61B 5/24; A61B 5/263; A61B 5/265; A61B 5/268; A61B 5/271; A61B 5/273; A61B 5/282; A61B 5/283; A61B 5/291; A61B 5/293; A61B 5/31; A61B 5/316; A61B 5/333; A61B 5/335; A61B 5/369; A61B 5/372; A61B 5/6867; A61B 5/6868; A61B 2562/125; A61N 1/0556; A61N 1/04; A61N 1/042; A61N 1/0526; A61N 1/0529; A61N 1/08; A61N 1/05

See application file for complete search history.

(56) References Cited

U.S. PATENT DOCUMENTS

| | | | |
|---|---|---|---|
| 9,549,708 B2* | 1/2017 | Mercanzini | A61B 6/506 |
| 9,808,613 B2* | 11/2017 | McDonald | A61N 1/057 |
| 2005/0065508 A1* | 3/2005 | Johnson | A61B 5/6852 |
| | | | 606/41 |
| 2006/0064150 A1* | 3/2006 | Heist | A61N 1/056 |
| | | | 607/122 |
| 2013/0282090 A1 | 10/2013 | Decre et al. | |
| 2016/0351292 A1 | 12/2016 | Toth et al. | |
| 2018/0169406 A1* | 6/2018 | Shah | A61N 1/04 |
| 2018/0229041 A1 | 8/2018 | Pepin et al. | |
| 2018/0333571 A1* | 11/2018 | Pepin | A61N 1/0556 |

FOREIGN PATENT DOCUMENTS

| | | | | |
|---|---|---|---|---|
| CN | 107106838 A | 8/2017 | | |
| EP | 1935449 | 6/2008 | | |
| JP | 2013505781 A | 2/2013 | | |
| WO | WO-02096482 A2 * | 12/2002 | ............... | A61N 1/05 |
| WO | WO-2008048237 A2 * | 4/2008 | ......... | A61B 5/04001 |
| WO | 2009137186 | 11/2009 | | |
| WO | WO-2009137186 A1 * | 11/2009 | .......... | A61B 5/0422 |
| WO | 2012139124 A1 | 10/2012 | | |

OTHER PUBLICATIONS

Application No. CN201980063360.7 , Office Action, Mailed on Feb. 7, 2024, 10 pages.

* cited by examiner

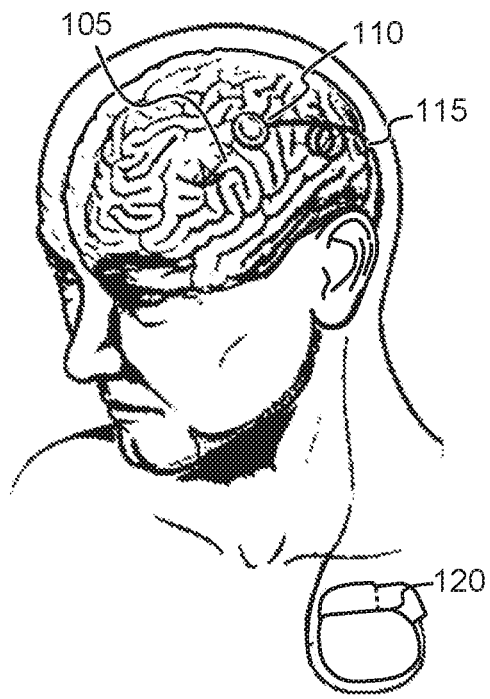
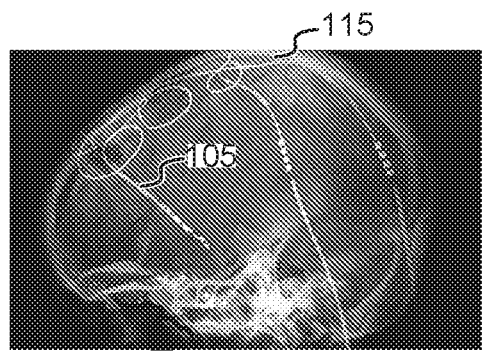
FIG. 1A  FIG. 1B
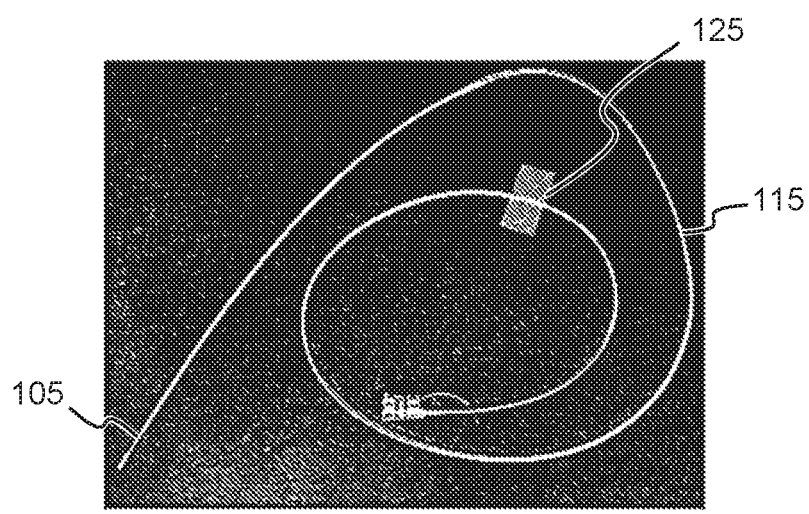
FIG. 1C

IMPLANTABLE MEDICAL DEVICES WITH MICROFABRICATED LEADS

CROSS-REFERENCE TO RELATED APPLICATIONS

This application is a 371 National Phase of International Patent Application No. PCT/US2019/052556 filed Sep. 24, 2019, which claims priority to U.S. Provisional Application No. 62/737,371 filed on Sep. 27, 2018. The disclosures of the above-named applications are incorporated by reference herein in their entireties.

FIELD OF THE INVENTION

Embodiments relate to an implantable device. Specifically, a device includes a flexible connection component that includes a set of conductive filaments that connect a set of electrodes (or traces connected to the electrodes) and circuitry that receives and/or transmits electronic signals from and/or to the electrodes.

BACKGROUND

Use of electrodes to detect electrical signals and/or deliver stimuli is becoming an increasingly popular diagnostic and/or therapeutic strategy. In some instances, one or more electrodes are included as part of an implant device, such that signals can be recorded and/or delivered chronically over an extended time period. Many traditional approaches for using electrodes in implant devices feature low-density electrode arrays of less than eight channels. However, recent improvements in microfabrication processing has enabled multiple electrodes to be disposed on a portion of the device to be positioned at a target location. For example, multiple electrodes may disposed along a length of a neural probe. One approach for using multiple electrodes is to design a device such that each electrode delivers a same stimulus. Manufacturing a multi-electrode device having independent electrode-associated channels requires constructing the device to ensure that the channels remain separate (to prevent shorting) across an entire length between the electrodes and associated circuitry. Given that intermediate components (e.g., that extend from circuitry outside of a person's scalp, skull and/or body to electrode traces) are frequently at least partly inside a person's body or brain, it is desirable that the intermediate components remain thin. Designing connections that can remain thin while maintaining channel separation can be particularly challenging when the number of electrodes is high.

SUMMARY

In some embodiments, an implantable medical device is provided that includes one or more electrodes, a flexible connection component, circuitry and one or more electrical interfaces. The flexible connection component can include a surface comprised of a set of filaments. The set of filaments can include multiple non-conductive filaments. The surface can include a set of conductive elements (e.g., conductive filaments, which can be included in the set of filaments). A set of electrical channels can extend across the flexible connection component. Each of the set of electrical channels can extend across at least one of the set of conductive elements and can be electrically connected with an electrode of the one or more electrodes. The circuitry can be configured to process recorded data transmitted over one or more of the set of electrical channels and/or to output control signals that identify stimulation parameters to be communicated over at least one of the set of electrical channels. Each electrical interface of the one or more electrical interfaces can be configured to connect an end of an electrical channel of the set of electrical channels with the circuitry.

In some embodiments, a method of manufacturing an implantable medical device is provided. Each of a set of filaments can be concurrently pulled from a corresponding filament spool. The pulled set of filaments can be positioned on a substrate in a braided or woven pattern. The set of filaments can include multiple conductive filaments and multiple non-conductive filaments. The multiple conductive filaments can be separated from each other by an insulating material or themselves each include an insulating coating. The substrate and positioned pulled set of filaments can be shaped to form a cylindrical shape. For each conductive filament of the multiple conductive filaments, a first end of the conductive filament can be connected to an electrode or trace connected to an electrode and a second end of the conductive filament can be connected to a bond pad.

BRIEF DESCRIPTION OF THE DRAWINGS

Illustrative embodiments of the present invention are described in detail below with reference to the following drawing figures:

FIGS. 1A-1C illustrate an implant device that can be used to record electrical signals and/or deliver electrical stimuli according to an embodiment of the invention.

DESCRIPTION

Figure 2:
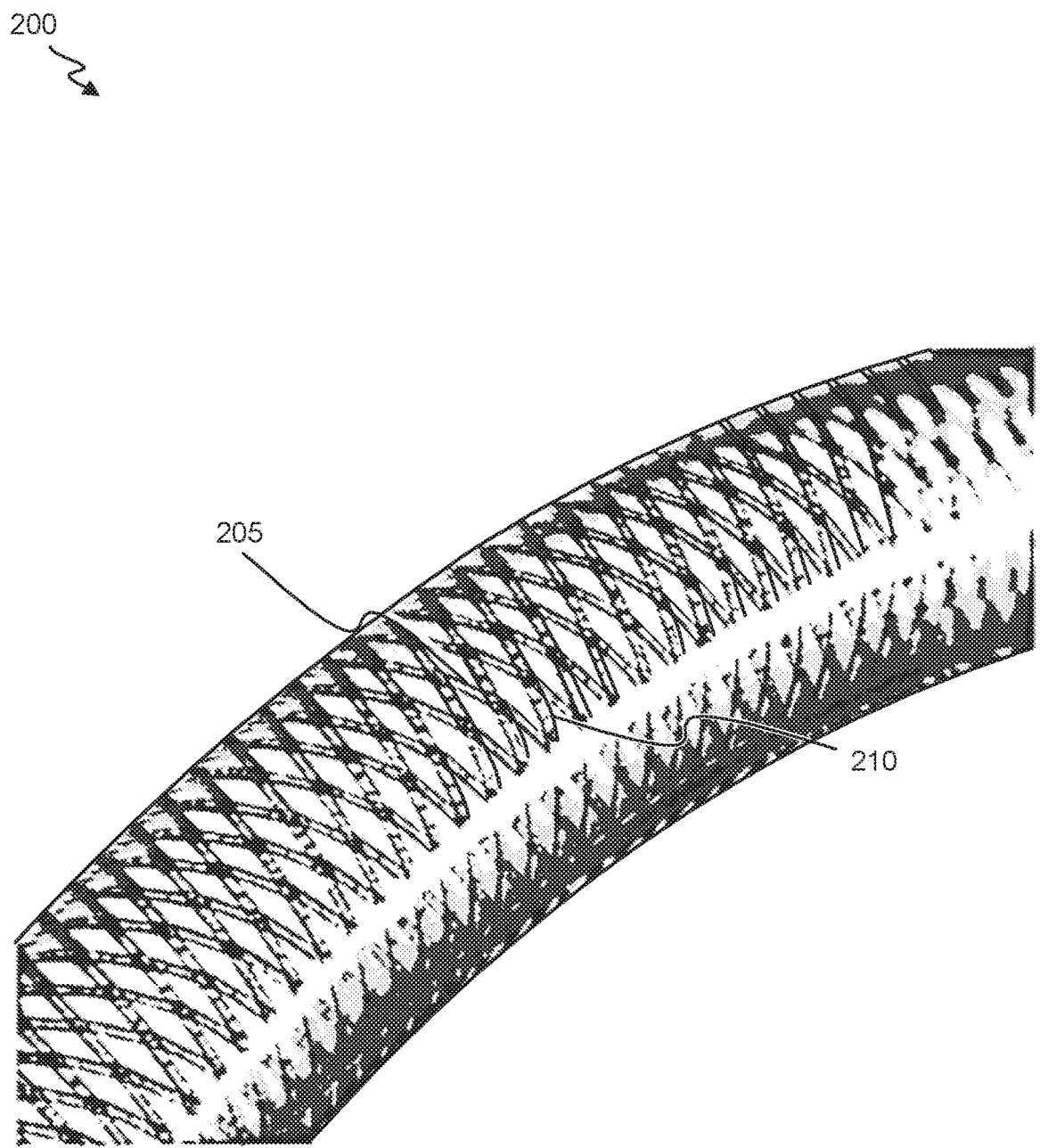
FIG. 2 illustrates a multi-filament connection component that can be included as part of an implant device according to an embodiment of the invention.

In some embodiments, an implant device is provided, along with methods for making and using the same. The implant device can include one or more electrodes along with a flexible connection component. The flexible connection component can include a cable (e.g., data cable), one or more leads and/or a catheter that connects the one or more electrodes to circuitry that receives data collected at the electrode(s) and/or that controls stimuli to be delivered at the electrode(s). Each connection that extends from a single channel to the circuitry can be referred to as an electrical channel. The flexible connection component can include a set of filaments, such as a set of microfilaments. The set of filaments can be positioned and/or configured to enable reliable communication across each electrical channel and to prevent shorting across multiple electrical channels. For example, the multiple conductive filaments can be separated from each other by an insulating material or themselves each include an insulating coating.

As one example, the flexible connection component can include a set of conductive filaments—each of which extends across the flexible connection component and being positioned such that there is a space (e.g., an empty space)

between each given conductive filament and all surrounding conductive filaments. This approach limits the density of electrical channels, due to the required spacing.

As another example, the flexible connection component can include a set of conductive filaments and a set of non-conductive filaments. The set of non-conductive can be positioned to separate, straddle or space adjacent conductive filaments. In some instances, the set of filaments are arranged in a braid, woven or grid pattern, with the set of conductive filaments running in a first direction different than a second direction in which the set of non-conductive filaments are running. For example, the set of non-conductive filaments can be positioned to extend in a direction that has a first angular offset from a central axis of the flexible connection component, and the set of conductive filaments can be positioned to extend in a different direction that has a second angular offset from the central axis. The set of conductive filaments and the set of non-conductive filaments may nonetheless be positioned within a same surface, such that each of the set of non-conductive filaments intersects with one, more or all of the set of conductive filaments.

As yet another example, the flexible connection component can include a set of coated conductive filaments. Each of the coated conductive filaments can include a conductive central filament and an insulating and/or dielectric thin coating. The set of coated conductive filaments can be arranged in a braid, woven or grid pattern. The coating can prevent or inhibit shorting between filaments.

In some instances, each filament of the set of filaments include a set of vias disposed across a length of filaments. Each via can be shaped and/or of a material to facilitate joining another via of another filament in a manner that restricts relative movement of the filaments thereafter. For example, the vias can be positioned to overlap or lock together, and then a bonding process can be performed.

Manufacturing the flexible connection component can include (for example) positioning the set of filaments on a flexible substrate. For example, conductive filaments may first be pulled from a first spool and non-conductive filaments may then be pulled from a second spool. The substrate and/or spools may be moved throughout the pulling process (e.g., and potentially between pulling the conductive and non-conductive filaments). A coating layer (e.g., that includes a thermoplastic or thermoset material) may be deposited over the filaments, and the substrate may then be rolled or folded into a target shape (e.g., a cylinder).

In some instances, the implant device includes a fixture that is positioned at or near an end of the flexible connection component. The fixture can include one or more engagement structures (e.g., holes, grooves or attachments)—each of which can be configured (e.g., shaped) to engage (e.g., partly or entirely surround or attach to) a filament to restrict movement of the conductive filament with respect to one or more dimensions. The fixture can thus help fix relative spacing of filaments and/or restrict relative movement between filaments, each of which can help avoid shorts between electrical channels. The fixture may further facilitate aligning ends of filaments with electrode traces to facilitate forming electrical connections. For example, each conductive filament can be electrically connected to an electrical trace that corresponds to an electrode at the fixture or at a position beyond the fixture. Each electrode can be connected to a corresponding trace by using ultrasonic welding, an epoxy, solder or crimping to attach the electrode to a bond patch connected to the trace. The fixture's engagement structures can thus provide precise relative locations of conductive filaments, such that bond pads can similar be precisely located (e.g., at or near the fixture). The location precision can allow bond pads to be more densely packed while still avoiding shorting between the electrical channels, which can allow devices to include higher numbers of electrodes and/or to include smaller dimensions relative to comparable devices that do not include features of the flexible connection component (and/or fixture(s)) as disclosed herein.

Some embodiments disclose herein refer to conductive filaments that extend across a length of a flexible connection component. It will be appreciated that alternative configurations are contemplated. For example, a single electrical channel can include multiple conductive filaments—each extending across a portion of the flexible connection filament.

FIGS. 1A-1C illustrate an implant device that can be used to record electrical signals and/or deliver electrical stimuli according to an embodiment of the invention. The depicted implant device includes a probe that includes one or more electrodes. The probe may (for example) have a median diameter that is greater than 0.1 mm, 0.5 mm, 1 mm or 2 mm and/or less than 1 mm, 2 mm, 3 mm or 5 mm. The probe may have a length that is (for example) greater than 5 cm, 10 cm or 20 cm and/or less than 25 cm or 15 cm. The probe can include a substrate that includes (for example) polyurethane and/or epoxy backfill. The probe can include, on one or more surfaces, one or more electrodes. Each of the one or more electrodes can include (for example) platinum or platinum iridium (e.g., with or without a TiN, iridium-oxide coating) The one or more electrodes can include (for example) a single electrode. The one or more electrodes can include (for example) more than: 1, 2, 4, 8, 16, 32 or 64 electrodes. The one or more electrodes can include (for example) less than 256, 128, 64, 32, 16, 8 or 4 electrodes. The electrodes may be arranged along one or more circumferential, vertical and/or horizontal lines and/or in a spiral configuration.

Probe 105 can further include one or more traces. In some instances, each of the one or more traces connects (physically and/or electrically) to a single electrode of the one or more electrodes and runs up (e.g., is positioned along a long axis of) the probe to terminate at a proximal end. Each trace can include a suitable conductor such as stainless steel, silver, copper or other conductive materials. Each trace may further include a coating or sheathing for anticorrosive, insulative and/or protective reasons.

Each of the traces can be (e.g., electrically and/or physically) connected to an interface 110 that is also connected to a flexible connection component 115. Interface 110 can include (for example) a structure that includes one or more engagement features configured electrically and physically connect probe 105 with flexible connection component 115.

Flexible connection component 115 can include a substrate (e.g., a dielectric substrate and/or a substrate comprising or composed of a polyurethane, polycarbonate, silicone, polyethylene, fluoropolymer and/or other medical polymers, copolymers and combinations or blends) and one or more electrical connections that connect the one or more electrodes to circuitry 120. For example, a pattern 125 of filaments can be formed on a planar substrate. Pattern 125 can include a set of conductive filaments—each at least partly connecting an electrode to circuitry 120. Pattern 125 can be subsequently shaped (e.g., rolled or wrapped) into a three-dimensional configuration. It will be appreciated that FIG. 1C shows an illustration where one portion of pattern 125 is unwrapped from to show its pattern, though pattern 125 can uniformly extend in a wrapped configuration across a length of flexible connection component 115.

Each conductive filament can have a length that is at least 3 cm, 5 cm, 10 cm or 50 cm and/or that is less than 150 cm, 100 cm, 50 cm or 25 cm. Each of the one or more electrical connections can include a conductive filament (e.g., a conductive microfilament). Pattern 125 can further include one or more non-conductive filaments, which may separate and/or space adjacent conductive filaments. In some instances, the (conductive and non-conductive) are braided, wound or disposed to form a pattern (e.g., a grid pattern). This type of configuration may result in individual non-conductive filaments intersecting with and/or contacting one or more conductive filaments while maintaining space between conductive filaments. Flexible connection component 115 can include one or more coating layers that further constrain the relative positions of the filaments.

Flexible connection component 115 may be flexible along its long axis. In some instances, flexible connection component 115 is rigid or has a degree of rigidity along a cross section perpendicular to its long axis such that at least a threshold amount of spacing between filaments (in particular, spacing between conductive filaments) is maintained to prevent shorting.

In some instances, each of the filaments in flexible connection component 115 includes a same material. For example, in some instances, each conductive filament and each non-conductive filament includes LCP, a dielectric material and/or an insulator. Conductive filaments may further include (for example) a top layer, pattern and/or sputtering that includes or is a conductive material. The conductive material can include or can be stainless steel, silver, copper or other conductive materials, which may have separate coatings or sheathing for anticorrosive, insulative and/or protective reasons.

Circuitry 120 can be configured to receive signals detected at the electrode(s) on probe 105 and/or to deliver electrical signals corresponding to stimuli to be delivered by the electrode(s) on probe 105. Circuitry 120 can include (for example) one or more circuits, chips, integrated circuits, wires, processors and/or computing devices. FIG. 1A shows circuitry 120 as being located outside of a person from in the implant device is implanted. It will be appreciated that, in some instances, circuitry 120 may be positioned inside a person (e.g., underneath a scalp) of a person in which the implant device is implanted. Circuitry 120 can include (for example) neurostimulation circuitry and/or a pulse generator, which can control a temporal pattern, duration and/or intensity of stimulation to be delivered at probe 105. In some instances, circuitry 120 identifies one or more stimulation parameters based on measured data (e.g., to operate in a closed-loop manner), such as signals recording by one or more sensing electrodes of probe 105 and/or other sensors measuring biological data.

In an implanted instance, probe 105 may be positioned such that the electrodes are positioned at or in (for example) the cortex, subcortex, thalamus (e.g., anterior nucleus of the thalamus, posterior thalamic region or ventrointermediate nucleus of the thalamus), hippocampus, zona incerta, pallidofugal fibers, globus pallidus internus, subthalmic nucleus, periaqueductal gray, and/or pons (e.g., tegmental nucleus of the pons). In the implanted instance, probe 105 may be fully or partly implanted into a person's brain, such that interface 110 may be outside or inside the person's brain and such that flexible connection component 115 may be fully or partly outside of a person's brain. Some or all of the part or entirety of flexible connection component 115 may nonetheless remain implanted (e.g., under the person's scalp but outside of the skull).

In some instances, each component of the implant device can be biocompatible. In some instances, all or part of flexible connection component 115 and all of probe 105 can be biocompatible.

It will be appreciated that the implant device can further include one or more additional components (e.g., a housing, feedthrough assembly and/or power source) and can have one or more additional properties, such as one described in U.S. Provisional Application No. 62/732,666, filed on Sep. 18, 2018, entitled "Monolithic Lead Assembly and Methods of Microfabricating a Monolithic Lead Assembly", which is hereby incorporated by reference in its entirety for all purposes.

It will be further appreciated that, while FIGS. 1A-1C depict a device that includes a neural probe, other configurations are contemplated. For example, as opposed to or in additional to including a probe, the implant device can include other types of stimulating and/or recording components, such as other types of neural interfaces. For example, the implant device may include a probe configuration and/or other electrode component that includes a planar, round or cylindrical substrate attached to one or more book electrodes, split cuff electrodes, spiral cuff electrodes, epidural electrodes, helical electrodes, probe electrodes, linear electrodes, neural probe, paddle electrodes, intraneural electrodes.

FIG. 2 illustrates a portion of a flexible connection component 200 that can be included as part of an implant device according to an embodiment of the invention. Flexible connection component 200 includes a set of conductive filaments 205 and a set of non-conductive filaments 210 on or near a surface of flexible connection component 200. In the depicted instance, an orientation of each of set of conductive filaments 205 is the same within the set but different than an orientation of each of set of non-conductive filaments 210.

The differential orientation can be achieved based on (for example) different orientation of source spools corresponding to material for set of conductive filaments 205 and set of non-conductive filaments 210 and/or different orientation of a substrate during times at which set of conductive filaments 205 and set of non-conductive filaments 210 are pulled.

Flexible connection component 200 can be manufactured to preserve relative orientation of set of conductive filaments 205 relative to each other, relative orientation of set of non-conductive filaments 210 relative to each other and/or relative orientation of set of conductive filaments 205 relative to each other (e.g., to prevent or inhibit shorting between conductive filaments). For example, each filament may be affixed and/or attached to a substrate to inhibit subsequent movement. As another example, a layer may be deposited on top of the filaments to inhibit subsequent movement. The layer may include (for example) a thermoplastic or thermoset material. As yet another example, a geometry of the conductive filaments and/or non-conductive filaments can be configured to inhibit movement (e.g., the conductive filaments and/or non-conductive filaments can include grooves to receive the other type of filament). As yet another example, each conductive filament can be bonded to a set of non-conductive filaments (or the reverse). (Select types of material bonds may be particular strong, such as bonds between two filaments, each including LCP at a connection site.) As yet another example, conductive vias and/or a bonding agent can be formed on positions of overlap between conductive filaments and non-conductive filaments, and the filaments can be connected through (for example) an electrical connection (e.g., welding or crimping) or bonding process. The use of conductive vias can facilitate using non-conductive filaments to restrict movement of conductive filaments without relying upon braiding or winding techniques. For example, the most or all of set of conductive filaments 205 (e.g., between any ends, fixtures and/or interfaces) may be positioned on top of each underlying non-conductive filament (or the converse).

In the depicted instance, flexible connection component 200 has a cylindrical (albeit curved) shape, in that cross sections perpendicular to the long axis are generally circular. In some instances, set of conductive filaments 205 and set of non-conductive filaments 210 are first deposited on a flat substrate. A coating layer may be applied and potentially the substrate may be dissolved. Set of conductive filaments 205 and set of non-conductive filaments 210 (e.g., and any other attached substrate and/or layer(s)) can then be shaped into a target shape (e.g., a cylindrical shape). For example, set of conductive filaments 205 and set of non-conductive filaments 210 (e.g., and any other attached substrate and/or layer(s)) can be rolled around a shaping structure. While around the shaping structure, a shape-fixation process may be performed, such as a curing process and/or a coating process. In some instances, the shaping structure may then be removed or dissolved.

In this instance, flexible connection component 200 is hollow in that includes space along the long axis of flexible connection component 200 under its surface. The hollowness may improve the flexibility of flexible connection component 200.

The configuration shown in FIG. 2 can provide advantages over (for example) traditional techniques not utilizing non-conductive filaments and/or manufacturing techniques that produce patterns of a sea of conductive filaments and/or a set of non-conductive filaments. For example, an alternative technique is to separate leads corresponding to different channels using insulation materials. However, this approach can add to the width of the device. Thus, a decision may be made as to whether to restrict a number of channels/electrodes or whether to risk potential damage to implant-associated tissue. Further, use of channel-separating insulation can risk occurrence of flex-fatigue after extended use of the device. However, configurations utilizing multi-fiber arrangement (e.g., disclosed herein) can support high numbers of channels while maintaining flexibility of the connection component and reducing the probability of and/or extent of flex fatigue.

Figure 3:
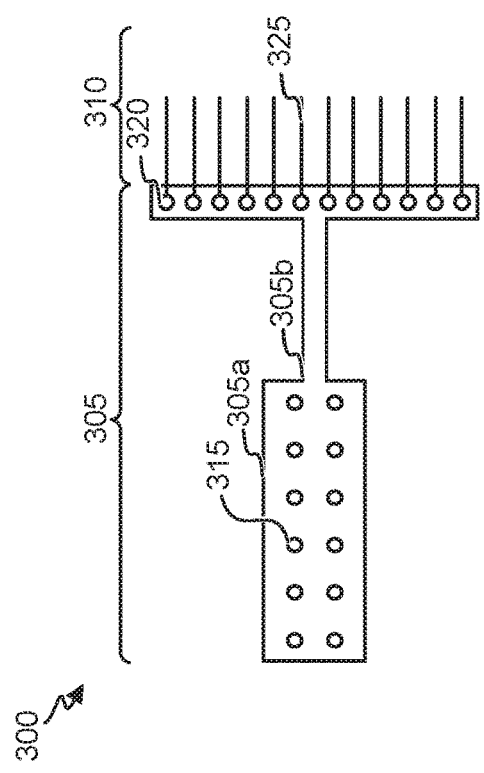
FIG. 3 illustrates a thin-film structure that includes filaments and electrodes according to an embodiment of the invention.

FIG. 3 illustrates a thin-film structure 300 that includes filaments and electrodes according to an embodiment of the invention. Thin-film structure 300 includes a neural-interface thin-film component 305 and a connection thin-film component 310. Thin-film structure 300 can have an average or maximum thickness that is (for example) less than 150 µm, 100 µm or 75 µm.

Neural-interface thin-film component 305 includes a set of electrodes 315. Each electrode 315 of the set can (for example) be conductive and/or include a metal or metal alloy. Each electrode 315 of the set can include (for example) platinum (Pt), platinum/iridium (Pt/Ir), copper (Cu), gold (Au), silver (Ag), gold/chromium (Au/Cr), titanium (Ti), gold/titanium (Au/Ti), or any alloy thereof. Each electrode 315 of the set may have a thickness (z) of from 0.1 µm to 50 µm, from 0.3 µm to 30 µm, from 0.5 µm to 20 µm, or from 1 µm to 15 µm. The set of electrodes 315 may be formed directly or indirectly on a substrate (e.g., a supporting structure), which can include an insulator and/or dielectric and may be non-conductive. Alternatively, the set of electrodes 315 may be formed indirectly on the substrate. The substrate can include (for example) polyurethane, polycarbonate, silicone, polyethylene, fluoropolymer, or another polymer, copolymer or blend.

Neural-interface thin-film component 305 may include a set of traces—each configured to communicate electrical signals between (e.g., in a unidirectional or bi-directional manner) an electrode and a conductive fiber in connection thin-film component. Each electrode may be connected to a trace directly or via an electrical contact and/or wiring layer. Each trace can include a conductive material and/or can be conductive. Each trace can include a pure metal, metal alloy, combination of metals (and/or of metal alloys), combination of metals and dielectrics, and so on. For example, each trace can include stainless steel, silver, gold, copper or gold/chromium. Each trace can further include a coating or sheathing for anticorrosive, insulative and/or protective purposes.

In some instances, neural interface thin-film component 305 includes a first portion 305a on which the set of electrodes 315 are positioned and a second portion 305b that lacks electrodes. A width of first portion 305a (corresponding to a vertical dimension in FIG. 3) may be larger than a width of second portion 305b. Traces connected to each electrode can extend across part of first portion 305a and across all of second portion 305b.

Each trace can connect to a bond pad 320. In some instances, one, more or all bond pads 320 can be conductive and can include (for example) copper, silver or gold. Connecting the trace to bond pad 320 can include (for example) welding the trace to bond pad 320 (e.g., using ultrasonic welding), using a conductive epoxy to connect the trace to bond pad 320, soldering the trace to bond pad 320, or welding the trace to bond pad 320.

Connection thin-film component 310 can include a set of conductive filaments 325. Each conductive filament 325 can include (for example) a metal, metal alloy or other conductive material. In one instance, each conductive filament 325 includes a nickel alloy (e.g., MP35N). Each conductive filament 325 can have a size corresponding to a French gauge of less than 1 French, less than 0.75 French or less than 0.5 French.

Each conductive filament 325 can be connected to a corresponding bond pad 320. Connecting conductive filament 325 to bond pad 320 can include (for example) welding conductive filament 325 to bond pad 320 (e.g., using ultrasonic welding), using a conductive epoxy to connect conductive filament 325 to bond pad 320, soldering conductive filament 325 to bond pad 320, or welding conductive filament 325 to bond pad 320.

In some instances, an insulating material (e.g., LCP) is disposed between bond pads 320, which can reinforce connection thin-film component. Conductive filaments 325 may include a same and/or different insulating material. For example, an insulating material can coat an entire flexible connection component with an insulating material (e.g., a same insulating material as that disposed between bond pads 320). Disposing the insulating material between bond pads 320 can result in bonding between the insulating material and conductive filaments 325 connected to bond pads. This bonding can increase stability of the position of conductive filaments 325. For example, each of the insulating material and conductive filaments 325 can include LCP, which can result in LCP-LCP bonding, which has very strong bond strength.

In the depicted instance, each conductive filament 325 is disposed to extend in a substantially straight line parallel to what will be the central axis of the device. Thus, in instances in which connection thin-film component 310 is rolled or wrapped to form a cylindrical shape, each conductive filament 325 can be at a substantially same angular position within any cross section taken along the central axis.

Part or all of thin-film structure 300 can be manufactured on one or more thin-film substrates and (in some instances) subsequently shaped into a three-dimensional shape. In one instance each of neural-interface thin-film component 305 and connection thin-film component 310 are manufactured on a separate substrate and separately shaped into a three dimensional shape (e.g., such that first portion 305a of neural-interface thin-film component 305 forms a first cylinder and connection thin-film component 310 forms a second cylinder). Bonding can then be performed to connect the two shaped components.

For example, the traces may be connected to bond pads 320 while in a planar configuration, neural-interface thin-film component 305 can then be spatially configured (e.g., wrapped around a cylindrical support), and conductive filaments 325 (e.g., which may also be configured in a three-dimensional shape) then be bonded to bond pads 320. As another example, conductive filaments 325 may be connected to bond pads 320 while in a planar configuration, connection thin-film component 310 can then be spatially configured (e.g., wrapped around a cylindrical support), and the traces can then be bonded to bond pads 320 (e.g., while neural-interface thin-film component 305 is configured in a three-dimensional shape). As yet another example, each of neural-interface thin-film component 305 and connection thin-film component 310 can be configured to include a three-dimensional (e.g., cylindrical) shape, and the traces and conductive filaments 325 may then be connected to bond pads 320.

An implant device can include a fixture to facilitate forming bondings between the traces and conductive filaments. For example, a fixture can have a shape corresponding to a strip, gear-shape or having a circular shape (or oval, square or rectangular shape). The fixture can include a set of grooves around a circumference or perimeter. As another example, a fixture can include a set of holes. The fixture can include a single planar configuration (e.g., that includes the grooves and/or holes) or may include two or more parallel surfaces (e.g., each including a set of grooves and/or holes). In the latter instance, the fixture may include channels (e.g., extended grooves along a distance or an extended tube-shaped hole) extending between spatially corresponding grooves and/or holes, of the parallel surfaces may primarily be separated by empty space (e.g., aside from one or more small mechanically connecting structures). A shape, size and/or diameter of each groove and/or hole can be configured to receive a conductive filament and/or trace.

In some instances, each of neural-interface thin-film component 305 and connection thin-film component 310 can be rolled or wrapped to form a cylindrical shape. Connection thin-film component 310 can be positioned such that each conductive filament 325 is positioned to be engaged with (e.g., within) a groove or hole in a fixture. Neural-interface thin-film component can include bond pads 320 and can be positioned such that bond pads 320 align with the grooves or holes in the fixture. Conductive filaments 325 can then be bonded to bond pads 320, thereby electrically connecting traces to conductive filaments 325. In some instances, an insulating material (e.g., LCP monofilament) is then disposed between bond pads 320.

The connection can be further reinforced with (for example) or silicone. In some instances, a tube (e.g., polyurethane tube) is positioned over bond pads 320 and the tube is then backfilled with an insulating or adhesive material or silicone.

It will be appreciated that opposite ends of conductive filaments can be connected with circuitry. The connection may further include use of bond pads and/or a fixture to facilitate alignment and/or stabilization of conductive filaments 325.

Figure 4:
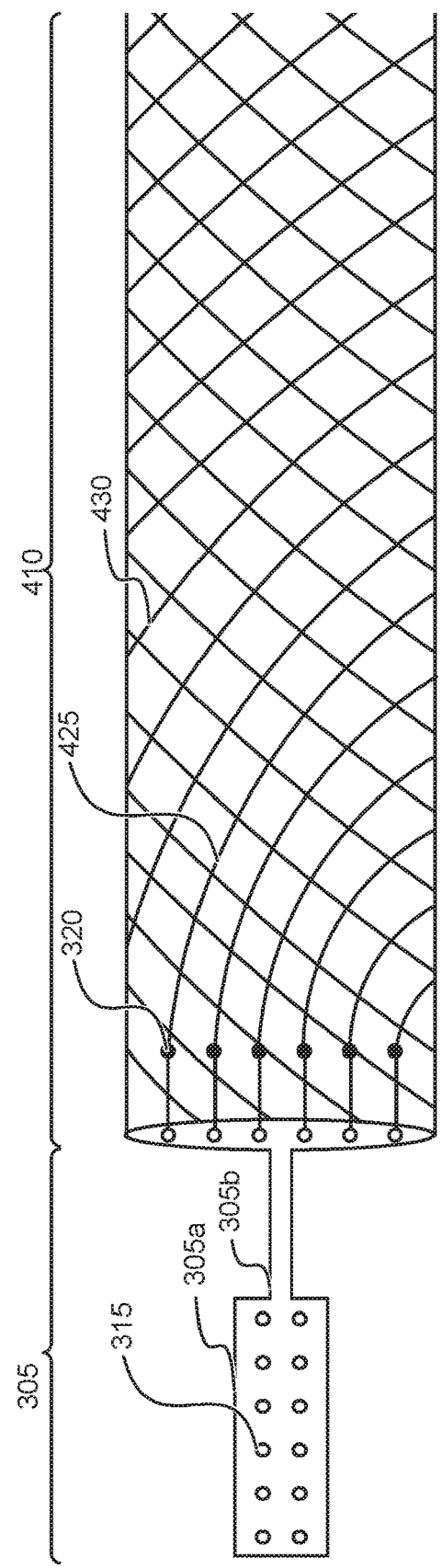
FIG. 4 illustrates a thin-film structure that includes filaments and electrodes according to an embodiment of the invention.

FIG. 4 illustrates a thin-film structure 400 that includes filaments and electrodes according to an embodiment of the invention. Thin-film structure 400 includes many features that parallel corresponding features shown in FIG. 3. However, thin-film structure 400 includes a connection thin-film component 410 that includes conductive filaments 425 that are oriented in a direction that is not parallel to a center long access of the implant device. Further, connection thin-film component 410 includes a set of non-conductive filaments 430. Each conductive filament 425 can cross multiple non-conductive filaments 430.

In some instances, each of the set of conductive filaments 425 and each of the set of non-conductive filaments 430 includes a same material, such as a same polymer. For example, each conductive filament and non-conductive element can include an insulating material. The conductive filaments can further include conductive material (e.g., sputtered or coats onto the insulating material). Using a same material in the conductive and non-conductive filaments can facilitate fixing relative positions of the filaments. For example, each conductive filament and each non-conductive filament can include LCP. The filaments can then be bonded together at their intersecting positions, which—due to the shared LCP material—can result in strong bonding between the filaments.

Each conductive filament 425 and/or each non-conductive filament 430 can have a size corresponding to a French gauge of less than 1 French, less than 0.75 French or less than 0.5 French and/or approximately 0.15 mm. Each conductive filament 425 may, but need not, have a diameter that is substantially the same as the diameter of the non-conductive filaments 430.

In some instances, conductive filaments 425 and non-conductive filaments 430 are disposed while the substrate is in a three-dimensional shape. For example, the filaments may be disposed on a cylindrical substrate.

The filaments can be disposed such that (for example), at each cross-section of the device portion that includes connection thin-film component 410 and along a center axis of the device, each conductive filament is either intersecting with a non-conductive filament or is situated such that the closest filament on each side of the conductive filament is a non-conductive filament. In some instances, connection thin-film component 410 includes a cross section (e.g., which can include a cross-section associated with an end of the filaments) at which adjacent filaments are equally spaced and in an alternating pattern between conductive and non-conductive filaments exists.

Conductive filaments 425 and non-conductive filaments 430 can be positioned in a braid or wound configuration. The positioned filaments can be disposed across, rolled or wrapped to partly surround or form a surface of a cylindrical or tubular component (e.g., similar to a catheter or lead).

In some instances, a preliminary connection component can be provided that includes a fixture (e.g., that includes a set of grooves and/or holes for engaging filaments) and a set of non-conductive filaments 430 engaged within a first subset of grooves and/or holes of the fixture. Bond pads 420 can be positioned at, within or near a second subset of the grooves and/or holes, and conductive filaments 425 can then be pulled to contact the bond pads and become engaged within a second subset of the grooves and/or holes.

Conductive filaments 425 can be bonded to (e.g., conductive) bond pads 420 using (for example) ultrasonic welding, epoxy, solder or crimping. Non-conductive filaments 430 can be bonded to (e.g., non-conductive) bond pads 420 using thermosetting and/or epoxy. Thus, bond pads 420 in FIG. 4 may include a subset that are non-conductive bond pads and a subset that are conductive bond pads.

The incorporation of non-conductive filaments can support a more dense spacing of filaments. In some instances, a maximum spacing between adjacent filaments (which can correspond to spacing between conductive filaments and/or spacing between parallel filaments) can be less than 100 μm, less than 50 μm or less than 30 μm and/or can be approximately 20 μm. Thus, in some instances, the filament configuration can facilitate manufacturing an implantable device that includes at least 128, at least 64 or at least 32 electrodes but nonetheless has a maximum width across probe 305 and connection thin-film component 410 (when in its final shape, such as being rolled into a cylindrical shape) of 1.7 mm. In some instances, the filament configuration can facilitating manufacturing an implantable device that includes less than or equal to 8, 4, 2 or 1 electrode(s) but has a maximum width across probe 305 and connection thin-film component 410 (when in its final shape, such as being rolled into a cylindrical shape) of 1 mm or 0.5 mm.

Figure 5:
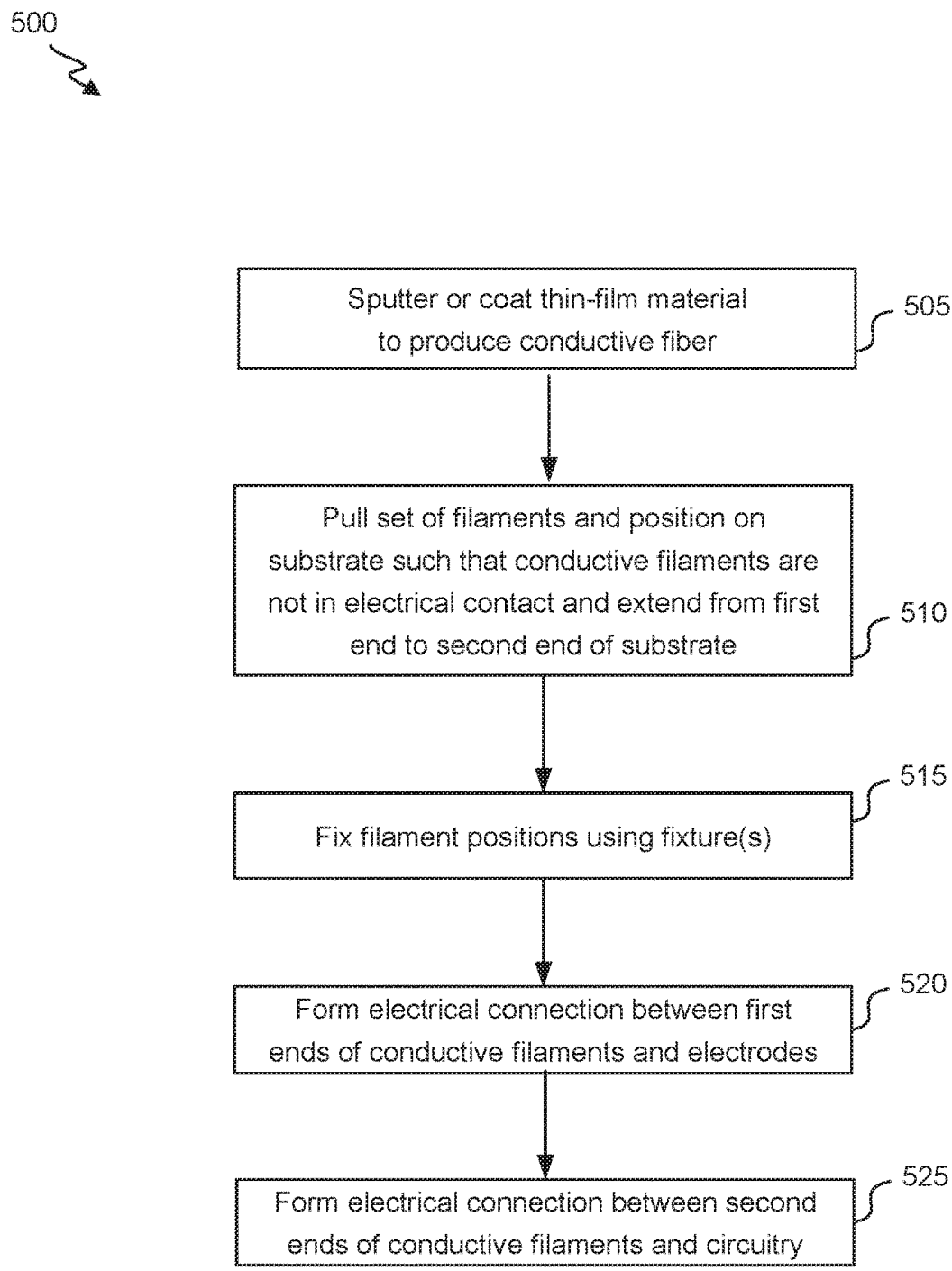
FIG. 5 shows a flowchart of a process for manufacturing an implant device according to an embodiment of the invention.

FIG. 5 shows a flowchart of a process 500 for manufacturing an implant device according to an embodiment of the invention. Process 500 can begin at block 505 where a thin-film material is sputtered or coated with a conductive material. For example, the thin-film material can include an LCP monofilament fiber. The conductive material can include (for example) stainless steel, silver or copper. In some instances, subsequent to (e.g., immediately following) the sputtering or coating, the conductive fiber is wound onto a spool.

At block 510, a set of filaments are pulled and positioned on a substrate. The set of filaments can include multiple conductive filaments (e.g., pulled from the conductive fiber) and multiple non-conductive filaments. The conductive filaments and non-conductive filaments may be pulled at separate times. In some instances, the substrate is moved while the filaments are being pulled, so as to control a direction along which the filaments run. The conductive filaments can be pulled to orient at a first angle relative to a long axis of the substrate and the non-conductive filaments can be pulled to orient at a second angle relative to the long axis of the substrate. In some instances an orientation angle of the conductive filaments is opposite to an orientation angle of the non-conductive filaments (e.g., 20° versus −20°). An absolute value of the angle of orientation of the conductive filaments and/or the non-conductive filaments may be less than (for example) 60°, 40° or 20°. The filaments can be pulled such that the non-conductive filaments are parallel to each other and such that the conductive filaments are parallel to each other.

The filaments can be pulled such that each of the set of filaments extends from a first end of the substrate to a second end of the substrate (e.g., where the first end and second end are at different positions with respect to a long axis of the substrate). The filaments can be pulled such that conductive filaments are not in electrical contact with each other. The filaments can be pulled such that each conductive filament intersects with one or more non-conductive filaments (e.g., where the intersection positions are different when intersecting with multiple non-conductive filaments). In some instances, with respect to each conductive filament, the conductive filament intersects a non-conductive filament at at least 4, 8 or 16 positions along its length. It will be appreciated that, in some instances, a conductive filament and non-conductive filament can intersect multiple times.

At block 515, one or more fixtures can be used to at least partly fix or restrict movement of filament positions. For example, a fixture can be positioned at or next to each end of the substrate. The fixture can include a set of holes and/or grooves—each shaped to receive a filament (e.g., having a width or diameter that is larger than a width of a corresponding filament and/or having a width or diameter that is less than about 300%, less than 200% or less than 150% a width of a correspond filament). Each filament can be positioned within a groove or hole. Each groove or hole can further support or be adjacent to a structure to which the filament is to be attached (e.g., a bonding pad). Ends of filaments can be attached to grooves and/or holes within the fixture via (for example) bonding, welding, thermosetting, an adhesive, etc.

At block 520, for each conductive filament, an electrical connection is formed between a first end of the conductive filament and an electrode. In some instances, block 520 includes bonding the filament with a bonding pad positioned at or near a groove of the fixture (e.g., in which case, the bonding may both fix the filament position and form the electrical connection). In some instances, block 520 includes bonding electrode traces with a bonding pad and/or otherwise connecting them with the conductive filaments. In some instances, an end of a conductive filament may extend through a groove or hole of the fixture, and block 520 can then include bonding the end with a bonding pad.

At block 525, for each conductive filament, an electrical connection is formed between a second end of the conductive filament and circuitry. In some instances, block 525 includes bonding the filament with a bonding pad positioned at or near a groove of the fixture (e.g., in which case, the bonding may both fix the filament position and form the electrical connection). In some instances, block 525 includes bonding connections to circuitry with a bonding pad and/or otherwise connecting them with the conductive filaments. In some instances, an end of a conductive filament may extend through a groove or hole of the fixture, and block 525 can then include bonding the end with a bonding pad.

In some instances, the substrate is flat and planar when the filaments are pulled. In some instances, the substrate is non-planar and/or supported by a three-dimensional supporting structure. For example, the substrate may be positioned around a cylindrical support, which may be rotated and/or moved along a long and/or horizontal axis as fibers are being pulled. In instances where the substrate is flat and planar when the filaments are pulled, the substrate can subsequently be wrapped or shaped to form a three-dimensional shape (e.g., wrapped around a cylindrical support). In instances in which a support is used while or after filaments are being pulled, the support may remain under the substrate or may be subsequently removed (e.g., after a coating layer is applied on the filaments and/or various intersections are bonded, such as intersections between conductive and non-conductive filaments and/or intersections with a non-conductive or conductive filament and a bond pad).

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

It is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure.

While the principles of the disclosure have been described above in connection with specific apparatuses and methods, it is to be clearly understood that this description is made only by way of example and not as limitation on the scope of the disclosure.

What is claimed is:

1. An implantable medical device comprising:
    a thin film defining an array portion and a flexible connection portion;
    one or more electrodes disposed on the array portion;
    a set of filaments disposed on the flexible connection portion, the set of filaments including multiple non-conductive filaments, and multiple conductive filaments, wherein at least some of the multiple non-conductive filaments and the multiple conductive filaments are braided or woven together;
    a circuitry configured to process recorded data transmitted over one or more electrical channels of a set of electrical channels and/or to output control signals that identify stimulation parameters to be communicated over at least one of the set of electrical channels; and
    one or more electrical interfaces, wherein each electrical interface of the one or more electrical interfaces is configured to connect an end of an electrical channel of the set of electrical channels with the circuitry,
    wherein some of the conductive filaments are configured to electrically connect with a corresponding electrode to operate as an electrical channel of the set of electrical channels and transmit data from the electrode to the circuitry and/or output control signals from the circuitry to the electrode, and
    wherein each of the multiple conductive filaments includes multiple monofilament fibers, each of the multiple monofilament fibers includes a non-conductive core formed from a thin-film material with a conductive material disposed on the thin-film material.

2. The implantable medical device of claim 1, wherein the multiple monofilament fibers are positioned so as to not overlap with each other.

3. The implantable medical device of claim 1, wherein the set of electrical channels includes at least 64 channels.

4. The implantable medical device of claim 1, wherein the conductive material includes:
    a sputtered conductive material and/or a conductive coating.

5. The implantable medical device of claim 1, wherein, for each of one or more braids, the at least one of the multiple monofilament fibers is bonded with the at least one of the multiple non-conductive filaments.

6. The implantable medical device of claim 1, wherein a material of the multiple non-conductive filaments is the same as the non-conductive core.

7. The implantable medical device of claim 1, wherein a material of the multiple non-conductive filaments is the same polymer material as the non-conductive core.

8. The implantable medical device of claim 1, further comprising a fixture that is positioned at or near an end of the flexible connection portion, the fixture including one or more engagement components, each engagement component of the one or more engagement components engaging a filament of the set of filaments to restrict movement of the filament.

9. The implantable medical device of claim 8, wherein:
    the one or more electrical interfaces include a set of bond pads at or near the fixture; and
    each of the multiple monofilament fibers is attached to a single bond pad of the set of bond pads.

10. The implantable medical device of claim 1, wherein:
    the flexible connection portion has a cylindrical shape;
    the flexible connection portion is hollow; and each of the set of filaments is positioned to run substantially along a length of the cylindrical shape that is perpendicular to a substantially circular cross-section of the cylindrical shape.

11. The implantable medical device of claim 1, wherein the flexible connection portion further includes a coating layer that wraps around the flexible connection portion across part or all of a length of the flexible connection portion.

12. The implantable medical device of claim 1, wherein the filaments of the set of filaments are disposed on an outer surface of the thin film.

13. The implantable medical device of claim 1, wherein:
    each of the multiple conductive filaments is electrically connected to an electrode of the one or more electrodes.

14. The implantable medical device of claim 1, wherein each of the set of filaments has a diameter that is less than 0.2 mm.

15. The implantable medical device of claim 1, wherein:
    each filament of the set of filaments includes a via extending across a length of the filament, and
    the filaments of the set of filaments are positioned such that, for each filament of the set of filaments, a via of the filament engages a via of at least one other filament of the set of filaments.

16. A method of manufacturing an implantable medical device, the method comprising:
    providing a thin film defining an array portion and a flexible connection portion;
    providing one or more electrodes disposed on the array portion;
    providing a set of filaments including multiple non-conductive filaments and multiple conductive filaments, wherein each of the multiple conductive filaments includes multiple monofilament fibers, each of the multiple monofilament fibers includes a non-conductive core formed from a thin-film material with a conductive material disposed on the thin-film material;
    concurrently pulling each filament of the set of filaments from a corresponding filament spool to position a pulled set of filaments on the flexible connection portion of the thin film, wherein at least some of the multiple non-conductive filaments and the multiple conductive filaments are braided or woven together and positioned such that the conductive filaments do not overlap with each other;
    providing a circuitry to process recorded data transmitted over one or more electrical channels of a set of electrical channels and/or to output control signals that identify stimulation parameters to be communicated over at least one of the set of electrical channels;

shaping the thin film and the positioned pulled set of filaments to form a cylindrical shape; and for each of the multiple conductive filaments:
- forming an electrical connection between a first end of the conductive filament and a corresponding electrode of the one or more electrodes to operate as an electrical channel of the set of electrical channels and transmit data from the corresponding electrode to the circuitry and/or output control signals from the circuitry to the corresponding electrode; and
- forming an electrical connection between a second end of the conductive filament and the circuitry via a corresponding electrical interface of one or more electrical interfaces.

17. The method of claim 16, further comprising:

forming a coating layer on the positioned set of filaments, wherein the coating layer includes a thermoplastic or thermoset material.

18. The method of claim 16, further comprising:

bonding at least some of the positioned set of filaments together to fix the braided or woven pattern.

\* \* \* \* \*